US004001760B2

United States Statutory Invention Registration [19]

[11] Reg. Number: H1760

Elango et al. [45] Published: Nov. 3, 1998

[54] PROCESS FOR GLYCOL ESTERS OF AN ALKALI METAL SALT OF 5-SULFOISOPHTHALIC ACID

[75] Inventors: Varadaraj Elango, Charlotte, N.C.; William R. Lee, Coventry, R.I.; Jeffrey S. Hurley, Cornelius; Cheryl A. Littau, Charlotte, both of N.C.

[73] Assignee: Hoechst Celanese Corporation, North Somerville, N.J.

[21] Appl. No.: 780,474

[22] Filed: Jan. 8, 1997

[51] Int. Cl.[6] ..... C07L 311/00

[52] U.S. Cl. ..... 560/14

[58] Field of Search ..... 560/14

[56] References Cited

U.S. PATENT DOCUMENTS 3,018,272 1/1962 Griffing et al. .

3,936,389 2/1976 King et al. ..... 252/182

*Primary Examiner*—Charles Jordan

*Assistant Examiner*—Meena Chelliah

*Attorney, Agent, or Firm*—Scott E. Hanf

[57] ABSTRACT

A process for preparing bis alkylene glycol esters of an alkali metal salt of 5-sulfoisophthalic acid. The subject compound is useful in preparing modified polyesters which can be dyed with basic or cationic dyes. The process is economical and low cost since intermediate reaction products are not purified.

8 Claims, No Drawings

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

PROCESS FOR GLYCOL ESTERS OF AN ALKALI METAL SALT OF 5-SULFOISOPHTHALIC ACID

BACKGROUND OF THE INVENTION

1. Technical Field

This invention is direct to the field of monomers for cationic dyeable polyesters.

2. Background

Polyester fibers based on the polyesterification of terephthalic acid and alkylene glycols are well known. Polyester fibers are important textile fibers but they are difficult to dye by normal dyeing techniques and are generally dyed using disperse dyes. However, polyester fibers can be rendered dyeable by basic and acid dyes by incorporating a modifying monomer into the polyester chain.

Suitable monomers for rendering a polyester dyeable by a cationic or basic dyes are the bis glycol esters of the sodium salt of 5-sulfoisophthalic acid. U.S. Pat. No. 3,936,389 describes the use of sulfonated monomers in preparing cationic dyeable polyester fibers and discloses that the preferred sulfonate is a bis ethylene glycol ester of the sodium salt of 5-sulfoisophthalic acid. The glycol ester is prepared from the dimethyl ester of the sodium salt of 5-sulfoisophthalic acid and ethylene glycol at 160° C. to 250° C. using an ester interchange catalyst; e.g. lithium acetate and calcium acetate.

U.S. Pat. No. 3,018,272 discloses the preparation of potassium 3,5 di(carbomethoxy) benzenesulfonate from sulfoisophthalic acid in a methanol-benzene solvent mixture. The methyl ester is used in transesterification reaction to prepare a cationic dyeable polyester.

The sodium salt of 5-sulfoisophthalic acid is commercially available and it may be used to prepare its bis glycol esters. However, the commercially available sodium salt is expensive, and attempts to prepare the bis ester by simple esterification proved unsuccessful. Additionally, this route is economically unattractive because of the cost of the commercially available acid. Commercially available bis glycol esters are prepared by transesterification using the dimethyl ester as a starting material. Furthermore, commercially available bis ethylene glycol esters of the sodium salt of 5-sulfoisophthalate are not pure compounds but rather mixtures containing about 60 to 75 percent of the bis ethylene glycol ester, about 20 to 25 percent of the mixed ethylene glycol / methyl ester and about 3 to 6 percent of the dimethyl ester. Under polymerization conditions methanol is split off from the mixed and dimethyl esters. The low boiling methanol causes processing and safety problems at the high polymerization and extrusion temperatures. The methanol must be removed from the polymer melt without discharge to the atmosphere which presents an additional environmental problem. It is estimated that methanol recovery from a direct esterification polyester production line could cost millions of dollars per year.

It is the object of this invention to provide a process for preparing methanol-free, bis glycol esters of 5-sulfoisophthalic acid alkali metal salts in high purity from isophthalic acid in a most economical way.

SUMMARY OF THE INVENTION

The invention is a process for preparing methanol-free, bis alkylene glycol esters of the alkali metal salts of 5-sulfoisophthalic acid in high purity at low cost from isophthalic acid without the purification of intermediate products. These glycol esters have the following general formnula:

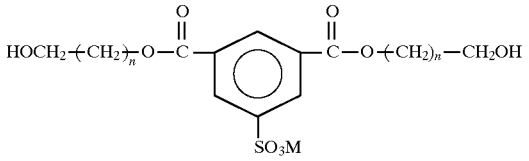

where: n is an integer independently selected from 1 to 10, preferably 1 to 3, and M is alkali metal moiety. The integer n is most preferably 1 and M is most preferably sodium. The alkylene glycol moiety may be either linear or branched if n is greater than 2, most preferably linear.

The process of the invention comprises sulfonating isophthalic acid and neutralizing the sulfo moiety with an alkali metal neutralizing agent, recovering the reaction products of the sulfonation reaction without purification, dispersing the reaction products of the sulfonation reaction in an alkylene glycol solvent; adjusting the pH of the reaction mixture, and esterifying the carboxylic acid groups of the 5-sulfoisophthalic acid alkali metal salt with said alkylene glycol solvent in the presence of a catalyst or without a catalyst. The bis alkylene glycol ester of the 5-sulfoisophthalic acid mono-alkali metal salt is separated from the alkylene glycol insoluble reaction products to provide a solution of bis glycol ester in glycol.

DESCRIPTION OF THE PREFERRED EMBODIMENTS

This invention is that of a high yield, cost effective process for producing a methanol-free, alkali salts of a bis alkylene glycol ester of 5-sulfoisophthalic acid from isophthalic acid. The preferred salt is the monosodium salt of the bis ethylene glycol ester of 5-sulfoisophthalic acid which is useful in the preparation of cationic dyeable polyester substrates.

The alkali salts of bis alkylene glycol esters of 5-sulfoisophthalic acid which may be prepared according to the process of the invention have the following general formula:

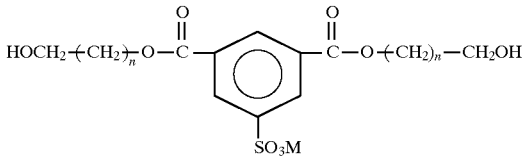

wherein: n is an integer independently selected from 1 to 10 and M is an alkali selected from lithium, sodium, potassium, and cesium. In the above formula n is preferably 1 to 3, most preferably 1 and M is preferably sodium or potassium, most preferably sodium. The alkylene glycol moiety may be either linear or branched if n is greater than 2, most preferably linear.

The invention provides a low cost, methanol-free, bis glycol ester because methanol based intermediates are not used and purification of intermediate reaction products is eliminated. Theoretically, commercially available sodium salt of 5-sulfoisophthalic acid can be used to prepare methanol-free bis alkylene glycol esters. However this commercially available starting material is expensive since it is purified after sulfonation to remove reaction by-products such as sodium sulfate, sulfuric acid, water, etc.

Additionally, very low yields were obtained by reacting ethylene glycol with the commercially available acid. Surprisingly, we have found that the insoluble, wet reaction products of the sulfonation and neutralization steps may be dispersed in a glycol solvent and the salt of the 5-sulfoisophthalic acid is esterified without purification. The esterified alkali metal salt of 5-sulfoisophthalic acid is then separated from the insoluble sulfonation reaction products to provide a solution of bis glycol ester in glycol.

The process of the invention comprises the following steps:

(a) sulfonating isophthalic acid at the 5-ring position;

(b) neutralizing the 5-ring position sulfo group with an alkali metal neutralizing agent;

(c) recovering the neutralized reaction products of step (b);

(d) dispersing said neutralized reaction products in a polyalkylene glycol;

(c) adjusting the pH of said dispersion to about 1.7 to 5;

(f) heating said dispersion to remove water and to form a bis glycol ester of said neutralized 5-sulfoisophthalic acid with or without catalyst and (g) separating said bis glycol ester from insoluble reaction products.

The sulfonation of isophthalic acid can be conducted according to methods well known in the art. Preferably, the sulfonation is conducted in oleum at a temperature from about 125° to 200° C., preferably from about 140° to 175° C. and most preferably about 150° to 160° C. The required reaction time will vary from 2 to 24 hours depending upon the reaction temperature and excess of sulfur trioxide. Generally 5 to 15 hours at 150° to 160° C. will produce satisfactory results.

The sulfonation is usually carried out in oleum, a mixture of concentrated sulfuric acid and sulfur trioxide. The reaction is carried out both with the commercially available oleum or by mixing concentrated sulfuric acid with sulfur trioxide during the reaction. Isophthalic acid and sulfuric acid are employed in a mole ratio ranging from about 1:1 to about 1:10, respectively with the preferred mole ratio being between 1:2 to 1:5. Although, one mole of sulfur trioxide is required to sulfonate one mole of the isophthalic acid to produce the product, it is preferred that an excess amount of sulfur trioxide be used in the reaction. Accordingly, the amount of sulfur trioxide should be in the range of 1.2 to 3 moles of sulfur trioxide per mole of isophthalic acid, preferably about 1.5 to 2. Alkali metal sulfates such as sodium sulfate or potassium sulfate may be added to the sulfonation reaction to improve quality and to minimize by-products. The amount of additives is in the range of mole ratios from about 1:0.01 to about 1:0.1.

After completing the sulfonation, the reaction mixture is cooled to room temperature and drown into an ice/water mixture at a temperature of about 0° to 80° C., preferably about 0° to 40° C., and most preferably about 0° to 20° C. The 5-sulfo ring substituent is neutralized using an alkali metal neutralizing agent such as lithium hydroxide, sodium hydroxide, potassium hydroxide, sodium carbonate, cesium hydroxide, sodium bicarbonate etc. The neutralizing agent is preferably a sodium or potassium base; most preferably sodium hydroxide or sodium carbonate. Approximately two equivalents of base are required to achieve neutralization of the 5-sulfo substituent due to the highly acidic nature of the reaction medium.

The neutralized 5-sulfoisophthalic acid salt will precipitate from the aqueous reaction medium. Preferably the reaction medium should be treated with salt such as sodium sulfate or sodium chloride to ensure complete precipitation. The precipitated product is then recovered by conventional methods such as filtration or centrifugation. The wet precipitate should not be washed due to the high solubility of the alkali metal salt of 5-sulfoisophthalic acid. When recovered by filtration, the filter cake contains about 2 to 10 percent inorganic salt ($M_2SO_4$), about 5–15 percent water, 2 to 5 percent sulfuric acid and about 65 to 90% percent of the alkali metal salt of 5-sulfoisophthalic acid product, wherein M is defined above.

The wet, acidic precipitate is esterified by slurrying or dispersing it in the desired alkylene glycol. The glycol employed is of the general formula $HO\text{-}CH_2\text{-}(CH_2)_n\text{-}OH$, where n is an integer from 1 to 10. A preferred glycol is ethylene or propylene glycol, most preferably ethylene glycol. Optionally a mixture of glycols may be used. The slurry should contain sufficient glycol to maintain fluidity and esterify the carboxylic acid functions of the 5-sulfoisophthalic acid salt. The alkali metal salt of 5-sulfoisophthalic acid and glycol are employed in a mole ratio ranging from about 1:2 to about 1:20 with the preferred mole ratio being 1:7 to 1:14.

The pH of the slurry is adjusted with a base such as sodium hydroxide or sodium carbonate to neutralize free acid in the slurry. In order to obtain an accurate pH measurement, it is desirable to dilute the pH test specimen with one part of distilled water per part of specimen prior to pH measurement. A relative pH of 1.7 to 5 provides satisfactory results; preferably the pH should be about 2 to 3. At a relative pH below 1.7, the reaction does not proceed in a satisfactory manner, i.e. the process gives erratic results—low yield and/or large amounts of undesired by-products.

The reaction mixture is heated to drive off residual water and after the water is removed the reaction mixture is heated to esterify the 5-sulfoisophthalic acid salt. Generally a temperature from about 155° to 220°0 C., preferably 170° to 200° C. gives acceptable results with removal of the water of reaction to drive the esterification to completion. The elevated temperature is maintained until the reaction is substantially completed as indicated by the cessation of the evolution of the water of reaction.

The esterification is carried out with or without a catalyst, preferably without a catalyst. Conventional esterification catalyst may be employed, such as an acetate salt of metals such as sodium acetate, calcium acetate, manganese acetate. If a catalyst is employed, the alkali metal salt of 5-sulfoisophthalic acid and catalyst are employed in a mole ratio ranging from about 20:1 to about 1000:1, preferably 50:1 to 200:1.

The bis glycol ester of the 5-sulfoisophthalic acid salt is soluble in the glycol and can be recovered from the insoluble inorganic salts produced in neutralizing the sulfonation medium. The inorganic salt-glycol-bis glycol ester mixture is viscous slurry at room temperature and it should be heated to improve the filtration or centrifugation to obtain the solution of bis glycol esters of the alkali metal salts of 5-sulfoisophthalic acid.

The following examples illustrate the invention.

EXAMPLE 1

Sulfonation of Isophthalic Acid with 30% Oleum

A 500 mL three neck flask fitted with a mechanical stirrer, thermometer, and a reflux condenser with dry tube was charged with 118.2 mL of 30% oleum, 6.0 g of sodium sulfate, and 83.0 g of isophthalic acid. The reaction mixture was heated to 155° C. and held at this temperature for 11 hours. The mixture was cooled to 25° C. and drowned into 500 g of ice and water. The solution was kept at 0°–20° C. with external cooling while 118.0 g of 50% sodium hydroxide was added. The precipitated product was isolated by filtration to give 147.5 g of material which contained 115.5 g (86% yield) of 5-sulfoisophthalic acid sodium salt.

EXAMPLE 2

Sulfonation of Isophthalic Acid with Sulfur Trioxide

A 300 mL autoclave was charged with 67.9 g of sulfuric acid 100%, 2.3 g of sodium sulfate and 33.2 g of isophthalic acid. The reactor was sealed and 29.1 g of sulfur trioxide was added to the reaction. The reaction mixture was heated to 155° C. and held at this temperature for 11 hours. The mixture was cooled to 85° C. and drowned into 220.0 g of ice and water. The solution was kept at 15°–20° C. with external cooling while 33.0 g of 50% sodium hydroxide was added. The product precipitated as a thick slurry. To complete the precipitation, 20 g of sodium sulfate was added. The product was isolated by filtration and 50.0 g of wet solids were collected which were found to contain 45.6 g of 5-sulfoisophthalic acid sodium salt.

EXAMPLE 3

Esterification of 5-Sulfoisophthalic acid Sodium Salt (SIPA) at pH 0.4

A 500 mL round bottom flask was charged with 300 mL ethylene glycol and 153.3 g of wet acidic cake containing 134.1 g of 5-sulfoisophthalic acid sodium salt. The pH of the slurry was found to be 0.4. About 0.8 g of manganese acetate was added and the reaction heated to reflux. The distillate was removed from the reaction mixture as the temperature rose to about 110° C. The temperature of the reaction did not rise above 140° C. The distillation was maintained for several hours until the solid product began to build up around the stirrer. The reaction mixture was cooled to room temperature and analyzed by HPLC. The HPLC analysis found that less than 2% product was formed. The distillate contained a large amount of ethylene glycol by-products. This example illustrates the necessity of adjusting the reaction mixture pH prior to esterification.

EXAMPLE 4

Esterification of 5-Sulfoisophthalic acid Sodium Salt (SIPA) at pH 1.0 without catalyst A 500 mL round bottom flask was charged with 300 mL ethylene glycol and 153.3 g of wet acidic cake containing 134.1 g of 5-sulfoisophthalic acid sodium salt. The pH of the slurry was determined to be 1.0. The reaction mixture was heated to reflux and the volatile components were distilled off as the temperature rose. When the reaction reached 195° C., the reaction mixture turned black and started to stick to the stirrer. In order to prevent the reaction product from further sticking to the stirrer, the reaction was stopped after several hours and cooled to room temperature. The HPLC analysis of the resultant solid revealed less than 5% product and many unidentified by-products. The distillate appeared to contain water and ethylene glycol by-products. Again a poor yield was obtained at low pH.

EXAMPLE 5

Esterification of 5-Sulfoisophthalic acid Sodium Salt (SIPA) at pH 1.6 without catalyst A 500 mL round bottom flask was charged with 300 mL ethylene glycol and 134.2 g of 5-sulfoisophthalic acid sodium salt obtained from a commercial vendor. The pH of the slurry was determined to be 1.6. The reaction mixture was heated to reflux and water was distilled off from the reaction mixture as the temperature rose. The distillation continued as the reaction was heated at 191° C. After 6 hours the product had turned brownish black and was beginning to stick to the stirrer. The mixture was cooled to room temperature. The HPLC analysis of the resultant solidified product revealed less than 5% 5-sulfoisophthalic acid bisethylene glycol ester and many unidentified by-products. The distillate appeared to contain water and ethylene glycol by-products. Again a poor yield was obtained at low pH.

EXAMPLE 6

Esterification of 5-Sulfoisophthalic acid Sodium Salt (SIPA) at pH 2.3 without catalyst A 1000 mL round bottom flask was charged with 600 mL of ethylene glycol and 307.2 g of wet acidic cake containing 268.2 g of 5-sulfoisophthalic acid sodium salt. The pH of the slurry was adjusted to 2.3 with 50% sodium hydroxide. The reaction mixture was heated to reflux and water was distilled from the reaction mixture as the temperature rose. The temperature was maintained at 195° C. for 6 hours. Residual sodium sulfate was removed by filtration at 65° C. to give 804.2 g of solution containing 302.7 g 5-sulfoisophthalic acid bisethylene glycol ester.

EXAMPLE 7

Esterification of 5-Sulfoisophthalic acid sodium salt (SIPA) at pH 2.7 with manganese acetate A 500 mL round bottom flask was charged with 300 mL of ethylene glycol and 268.1 g of wet acidic cake containing 134.2 g of 5-sulfoisophthalic acid sodium salt. The pH of the slurry was adjusted to 2.7 with 50% sodium hydroxide and 0.6 g manganese acetate was added. The reaction mixture was heated to reflux and water was distilled from the reaction mixture as the temperature rose. The temperature was maintained at 195° C. for 2 hours. The residual sodium sulfate was filtered off at 65° C. to give 414.2 g of solution containing 137.3 g of 5-sulfoisophthalic acid bisethylene glycol ester.

EXAMPLE 8

Esterification of 5-Sulfoisophthalic acid Sodium Salt (SIPA) at pH 2.7 with sodium acetate A 500 mL round bottom flask was charged with 300 mL ethylene glycol and 153.3 g of wet acidic cake containing 134.2 g of 5-sulfoisophthalic acid sodium salt. The pH of the slurry was adjusted to 2.7 with 50% sodium hydroxide and 0.64 g sodium acetate was added. The reaction mixture was heated to reflux and water was distilled from the reaction mixture as the temperature rose. The temperature was maintained at 195° C. for 4 hours. The residual sodium sulfate was filtered off at 65° C. to give 440.4 g of solution containing 151.7 g 5-sulfoisophthalic acid bisethylene glycol ester.

EXAMPLE 9

Esterification of 5-Sulfoisopbthalic acid Sodium Salt (SIPA) at pH 5.0 with manganese acetate A 500 mL round bottom flask was charged with 224 mL ethylene glycol and 114.2 g of wet material containing 100 g of 5-sulfoisophthalic acid sodium salt The pH of the slurry was adjusted to 5.0 with 50% sodium hydroxide and 0.4 g manganese acetate was added. The reaction mixture was heated to reflux and water was distilled from the reaction mixture as the temperature rose. The temperature was maintained at 195° C. for 2 hours. The residual sodium sulfate was filter off at 65° C. to give 301.0 g solution containing 66.4g 5-sulfoisophthalic acid bisethylene glycol ester.

The foregoing examples are intended to illustrate the process of this invention and should not be construed to limit the scope of this invention. Many variations in the process of this invention will be obvious to one of ordinary skill in the art and such obvious variations should not be construed to be beyond the scope of the claimed invention.

We claim:

1. A process for preparing a bis alkylene glycol ester of sodium-5-sulfoisophthalate which comprises:

(a) sulfonating isophthalic acid in the 5-ring position;

(b) neutralizing the 5-sulfo ring substituent with an alkali metal neutralizing agent;

(c) recovering the reaction products of said sulfonation and neutralizing steps;

(d) dispersing said reaction products in an alkylene glycol and adjusting the pH of said dispersion to about 1.7 to 5;

(e) heating said dispersion to the form the bis alkylene glycol ester of said neutralized 5-sulfoisophthalic acid and (f) separating said bis alkylene glycol ester from insoluble reaction products.

2. A process according to claim 1 wherein said alkylene glycol is selected from ethylene and propylene glycol.

3. A process according to claim 1 wherein said pH is about 2 to 3.

4. A process according to claim 2 wherein said alkylene glycol is ethylene glycol.

5. A process according to claim 4 wherein said pH is about 2 to 3.

6. A process according to claim 1 wherein said bis glycol ester is formed in the presence of an esterification catalyst.

7. A process according to claim 6 wherein said catalyst is sodium acetate.

8. A process according to claim 7 wherein said catalyst is manganese acetate.

* * * * *